US012642583B2

(12) United States Patent
Claude et al.

(10) Patent No.: US 12,642,583 B2
(45) Date of Patent: Jun. 2, 2026

(54) MULTIPURPOSE ELECTRODE

(71) Applicant: Boston Scientific Scimed, Inc., Maple Grove, MN (US)

(72) Inventors: John P. Claude, Redwood City, CA (US); Tom Saul, El Granada, CA (US); Amr Salahieh, Saratoga, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1404 days.

(21) Appl. No.: 16/300,407

(22) PCT Filed: Aug. 8, 2016

(86) PCT No.: PCT/US2016/046032
§ 371 (c)(1),
(2) Date: Nov. 9, 2018

(87) PCT Pub. No.: WO2017/024306
PCT Pub. Date: Feb. 9, 2017

(65) Prior Publication Data

US 2019/0117303 A1      Apr. 25, 2019

Related U.S. Application Data

(60) Provisional application No. 62/202,029, filed on Aug. 6, 2015.

(51) Int. Cl.
*A61B 18/14* (2006.01)
*A61B 18/00* (2006.01)

(52) U.S. Cl.
CPC *A61B 18/1492* (2013.01); *A61B 2018/00071* (2013.01); *A61B 2018/00107* (2013.01);
(Continued)

(58) Field of Classification Search
CPC ...... A61B 18/1492; A61B 2018/00214; A61B 2018/00755; A61B 2018/00875;
(Continued)

(56) References Cited

U.S. PATENT DOCUMENTS 5,830,213 A    11/1998  Panescu et al.
5,881,727 A     3/1999  Edwards
(Continued)

FOREIGN PATENT DOCUMENTS

CN      101969873 A    2/2011
CN      103379873 A    10/2013
(Continued)

OTHER PUBLICATIONS

Extended European Search Report issued in EP Application No. 16833999.2, mailed Jan. 3, 2019, 8 pages.
(Continued)

*Primary Examiner* — Joanne M Rodden
*Assistant Examiner* — Nora W Rhodes
(74) *Attorney, Agent, or Firm* — Nelson Mullins Riley & Scarborough LLP

(57)      ABSTRACT

Multi-purpose electrodes for use during ablation are provided. The electrodes comprise a variable impedance region and a relatively constant impedance region. The relatively constant impedance region can be used for mapping, and both regions can be used for ablating. The mapping region can obtain low frequency electrophysiological signals during mapping, while both regions can conduct higher frequency ablation electrical signals to a patient during ablation.

15 Claims, 4 Drawing Sheets

(52) U.S. Cl.
    CPC ............... *A61B 2018/00214* (2013.01); *A61B*
        *2018/0022* (2013.01); *A61B 2018/00577*
        (2013.01); *A61B 2018/00755* (2013.01); *A61B*
        *2018/00875* (2013.01); *A61B 2018/1465*
        (2013.01); *A61B 2018/1467* (2013.01)

(58) Field of Classification Search
    CPC .. A61B 2018/00107; A61B 2018/1465; A61B
        2018/00071; A61B 2018/0022; A61B
        2018/00577; A61B 2018/00839; A61B
        2018/1467
    USPC .......................................................... 606/41
    See application file for complete search history.

(56)              References Cited

U.S. PATENT DOCUMENTS

| | | | | |
|---|---|---|---|---|
| 6,134,463 | A | 10/2000 | Wittkampf et al. | |
| 6,233,491 | B1 | 5/2001 | Kordis et al. | |
| 6,391,024 | B1 | 5/2002 | Sun et al. | |
| 7,344,533 | B2 | 3/2008 | Pearson et al. | |
| 2005/0256521 | A1* | 11/2005 | Kozel ..................... | A61B 5/304 |
| | | | | 606/41 |
| 2006/0074411 | A1* | 4/2006 | Carmel .................. | A61B 18/16 |
| | | | | 606/32 |
| 2010/0204560 | A1 | 8/2010 | Salahieh et al. | |
| 2012/0292589 | A1* | 11/2012 | Yoneda .............. | G11C 13/0007 |
| | | | | 257/4 |
| 2013/0150693 | A1* | 6/2013 | D'Angelo ................ | A61B 6/12 |
| | | | | 601/3 |
| 2014/0357956 | A1 | 12/2014 | Salahieh et al. | |
| 2015/0182282 | A1* | 7/2015 | Zemel .................. | A61B 18/042 |
| | | | | 606/41 |
| 2017/0333125 | A1* | 11/2017 | Lepak .................. | A61B 1/0676 |

FOREIGN PATENT DOCUMENTS

| | | | | |
|---|---|---|---|---|
| WO | 2011143468 | A3 | 11/2011 | |
| WO | WO-2011143468 | A2 * | 11/2011 | ......... A61B 1/00082 |
| WO | 2013188640 | A1 | 12/2013 | |
| WO | 2014/068577 | A2 | 5/2014 | |
| WO | 2015/101787 | A2 | 7/2015 | |

OTHER PUBLICATIONS

International Preliminary Report on Patentability issued in PCT/US2016/046032, mailed Feb. 6, 2018, 5 pages.
International Search Report and Written Opinion issued in PCT/US2016/046032, mailed Oct. 24, 2016, 7 pages.

* cited by examiner

MULTIPURPOSE ELECTRODE

CROSS-REFERENCE TO RELATED APPLICATION

This application is a national phase application of PCT Application No. PCT/US2016/046032, internationally filed Aug. 8, 2016, which claims the benefit of U.S. Provisional Application No. 62/202,029, filed Aug. 6, 2015, the entire disclosures of which are incorporated by reference herein.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

When obtaining or monitoring electrophysiological measurements from a patient (which may be referred to as "mapping"), a small surface area electrode provides advantages, such as that there is less surface averaging of signals. This can result in more reliable measurements about the characteristics of the target tissue being mapped. Small surface area electrodes can also allow for monitoring of far and near field signals. Bigger electrodes can distinguish far field signals, but can have trouble distinguishing near field signals. Mapping can help determine what tissue should be ablated.

These small surface area electrodes can also be used to stimulate the tissue and measure a response. For example, after a line has been ablated, these electrodes can be used to stimulate tissue at an end of the line and monitor the signal at the other end of the line to determine efficacy of the ablation.

Large surface area electrodes provide an advantage for doing RF ablation in that fewer conductors are required to treat a given surface area and a large target area may be ablated in one pass, thereby reducing the time required to perform the ablation.

Since relatively larger surface area electrodes can be beneficial during ablation but less beneficial during mapping due to the greater surface area averaging, some relatively large surface area electrodes may be less than optimal when also used as mapping electrodes. Rather than using relatively large electrodes for both ablation and mapping, an alternative approach is to have one or more smaller mapping electrodes, and one or more relatively larger ablation electrodes. The mapping and ablation electrodes may be disposed on the medical device at different locations. In use, the mapping electrodes can obtain patient signals, and then the ablation electrodes can ablate tissue where the mapping suggests ablation should occur. If the device is not moved between the mapping and ablation steps, the location at which the ablation electrode contacts tissue is not the exact same as the location where the mapping electrode contacts tissue. In monopolar mode, for example, the ablation can occur at tissue different than the mapped tissue. If the device is moved after mapping to attempt to align the ablation electrode with the mapped tissue, it can be difficult to try to move the ablation electrodes to the same location as the mapped tissue, due to visualization challenges. Additionally, typically more than one mapping electrode is used to map tissue regions simultaneously, and the mapping results can indicate one or more target tissue locations to be ablated (either using monopolar or bipolar mode, or a combination thereof). This can further complicate attempting to ablate the desired tissue.

SUMMARY OF THE DISCLOSURE

In some embodiments, an electrode for use with an ablation catheter is provided. The electrode comprises a variable impedance region, wherein the variable impedance region has a first impedance when a first frequency is applied thereto, and a second impedance when a second frequency is applied thereto, the second impedance being different than the first impedance; and a substantially constant impedance region.

In some embodiments, the first impedance is higher than the second impedance when the first electrical signal has a lower frequency than the second electric signal. The first electrical signal can have a frequency of 1000 Hz or less, and the second electrical signal can have a frequency of at least about 50 KHz. In some embodiments, the substantially constant impedance region is adapted so that an impedance of the substantially constant impedance region does not vary based on the frequency of an electrical signal applied thereto. The variable impedance region can include a first layer of material disposed radially relative to a conductive electrode layer of material. In some embodiments, the first layer overlaps with only a portion of conductive electrode material, to create an overlap region where the two layers overlap, and a non-overlap region where the two layers do not overlap, when viewed in top view of the electrode. The non-overlap region can be disposed in a central portion of the electrode. The non-overlap region can be disposed in a peripheral region of the electrode. In some embodiments, the variable impedance region includes a layer of high dielectric material. The electrode can include more than one variable impedance region. In some embodiments, the variable impedance region is disposed in a peripheral region of the electrode. In some embodiments, the substantially constant impedance region is disposed within a central portion of the electrode. The electrode can be individually addressable. In some embodiments, a periphery of the electrode defines an uninterrupted electrode surface area that can be exposed to tissue to deliver an electrical signal to the tissue. The substantially constant impedance region can have an impedance lower than the first impedance or the second impedance. In some embodiments, the electrode is positioned on an expandable structure. The electrode can be configured to pass ablation energy at an ablation frequency through its entirety.

In some embodiments, an electrode is provided. The electrode comprises a physiological signal mapping section comprising a substantially constant impedance; and a tissue ablating section comprising the substantially constant impedance region and a variable impedance region, wherein the variable impedance region has a first impedance when a first frequency is applied thereto, and a second impedance when a second frequency is applied thereto, the second impedance being different than the first impedance.

The substantially constant impedance region can comprise a physiological signal mapping section. The electrode can include any of the features described above.

In some embodiments, an electrode is provided. The electrode comprises a first region and a second region, wherein, in the first region, the electrode comprises a layer of a variable impedance material disposed radially outward in a direction extending from a center of a conductive electrode layer of material to a periphery of the conductive electrode layer of material, and wherein, in the second region, the electrode does not comprise the layer of the variable impedance material.

The variable impedance material can comprise a high dielectric constant. In some embodiments, the first region is at least at a peripheral region of the electrode. The second region can be disposed at least at a central region of the electrode. The electrode can include any of the features described above.

In some embodiments, an electrode is provided. The electrode comprises a first conductive surface area when an electrical signal of at least 50 KHZ is applied thereto, and a second conductive surface area less than the first conductive surface area when an electrical signal of 1000 Hz or less is applied thereto. The electrode can include any of the features described above.

In some embodiments, a method of manufacturing a multipurpose electrode is provided. The method includes positioning a variable impedance material over only a first region of a conductive electrode material and not a second region of a conductive electrode material, to thereby create an electrode that includes a variable impedance region, the variable impedance region having a first impedance when a first frequency is applied thereto and a second impedance when a second frequency is applied thereto, the second impedance being different that the first impedance.

Positioning can comprise positioning the variable impedance material directly on the conductive electrode material. In some embodiments, positioning the variable impedance region comprises applying the variable impedance region using vapor deposition. The method can further comprise manufacturing the electrode such that it comprises any of the features described above.

In some embodiments, a method of using a multipurpose electrode is provided. The method comprises engaging an electrode with tissue within a patient; and obtaining an electrophysiology signal from the patient through a mapping region of the electrode without obtaining the electrophysiology signal from the patient through a variable impedance region of a tissue ablation region of the electrode.

In some embodiments, obtaining an electrophysiology signal from the patient comprises obtaining an electrophysiology signal that is 1000 Hz or less. The variable impedance region can have a first impedance when a first frequency is applied thereto, and a second impedance when a second frequency is applied thereto, the second impedance being different than the first impedance. The method can further comprise passing ablation energy through both the mapping region and the variable impedance region.

In some embodiments, a method of using a multipurpose electrode is provided. The method comprises engaging an electrode with tissue within a patient; and ablating tissue with a tissue ablation region of the electrode, wherein the tissue ablation region of the electrode has a surface area that is greater than a surface area of a mapping region of the electrode, and wherein the tissue ablation region includes the mapping region.

In some embodiments, ablating tissue comprises using the impedance of a variable impedance region of the tissue ablation region of the electrode. Ablating tissue can comprise delivering an electrical signal with a frequency of at least 50 KHz to the electrode.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
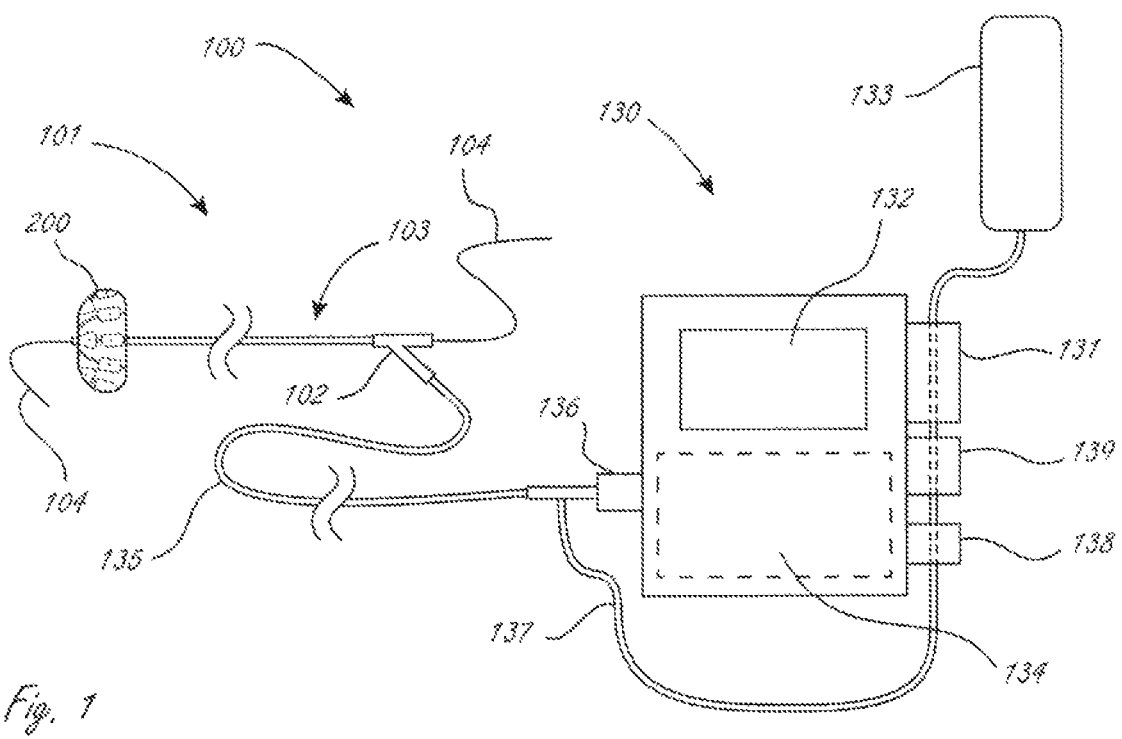
FIG. 1 illustrates an embodiment of an ablation system.

In some of the electrodes described herein, an exemplary benefit is that only a portion of the electrode (a mapping region) is adapted to obtain electrophysiological measurements from the patient during mapping, while a larger region of the electrode (an ablation region) is adapted to transmit ablation signals or energy to the patient. The electrodes can thus be thought of as multi-purpose or multi-functional, in that a single electrode can be effective as both a mapping electrode with a small area and as a larger ablation electrode. This can allow a relatively smaller region of the electrode to be used for obtaining signals (mapping) so as to reduce surface averaging of signals, while at the same time creating an ablation region of the electrode that is greater in surface area than the mapping region. This allows the mapping region to be set at any desired size or configuration, as well as allowing the ablation region to be set at any desired size or configuration. An additional benefit of the examples herein is that when desired a single electrode can be used to map tissue, and then ablate the same tissue as well as surrounding tissue (due to the larger ablation region), without having to move the device after the mapping has occurred.

Electrophysiological signals are relatively low in frequency and typically all important information is contained in frequencies below 1000 Hz and typically below 100 Hz. These are the low pass cut off frequencies generally used during mapping of electrophysiological signals. Stimulation and monitoring can also be performed at low frequencies (e.g., below 100 Hz, below 1000 Hz). RF ablations, however, are often performed at frequencies typically in excess of 50 KHz and more typically above 400 KHz particularly when treating atrial fibrillation. Thus the ablation is performed at a frequency much greater than the frequency of the signals obtained from the patient during mapping.

An exemplary variable impedance region includes a layer of high dielectric constant material. Dielectric constant is also commonly referred to as relative permittivity. In some embodiments all but a small portion of the electrode is covered with a thin layer of material having a high dielectric constant. At high frequencies the thin layer of dielectric provides a small increase in impedance, while at low frequencies it provides very high impedance. As such, during electrophysiology measurements (mapping) the uncovered section of electrode functions as a low impedance electrode to collect electrophysiological data, while the region of the electrode covered with the dielectric has high impedance and does not significantly interact in the performance of the circuit. During ablation, however, the dielectric covered region of the electrode provides a very low increase to impedance, and as such conducts the ablation energy to the tissue. During ablation the uncovered region of electrode also conducts the ablation signal to tissue, so the total region of ablation includes the uncovered electrode region and the covered region of the electrode. The ablation region of the electrode is thus larger than the mapping region of the electrode. A large surface area ablation electrode in the range of, for example, 0.02 sq. in. 0.2 sq. in., can thus be made to function as a smaller conductive surface area electrode at low frequencies and a large surface area electrode at high frequencies by covering all but a portion of the electrode with a thin layer of material having a high dielectric constant. Such an electrode performs as a multipurpose electrode.

An electrode constructed in such a fashion has particular advantage when used in any situation where it is desired to collect lower frequency electrophysiology data and perform RF ablations with the same electrode systems. Such a situation can occur in the performance of ablations to treat fibrillations of the heart in conjunction with the collection of electrophysiological data to inform the user as to where to target ablations and monitor the efficacy of the ablations performed.

Atrial fibrillation (AF) is an exemplary condition that would, if treated in this fashion, benefit from such an electrode configuration. The following describes one exemplary embodiment of a system capable of treating AF incorporating such electrode systems.

A detailed description of a merely exemplary embodiment of a system incorporating at least one multi-purpose electrode as described herein configured to treat atrial fibrillation follows. The overall system components need not be used together. For example, the exemplary energy generator can be used with a completely different type of mapping/ablation catheter. The system components are described together as an example only.

FIG. 1 illustrates an embodiment of an ablation system 100 that can be used for performing ablations to treat atrial fibrillation. The system is shown with the following components or features, but in some variations they need not all be present. A patient interface 101 includes an ablation balloon member 200 affixed to the distal end of an ablation catheter 103. The ablation catheter and ablation balloon comprise a guide wire lumen configured to track on a guide wire 104. A catheter interface cable 135 comprises an irrigation lumen, electronic conductors, and other features required to service the ablation balloon. The ablation balloon member 200 as depicted in FIG. 1 comprises a plurality of multipurpose electrodes 210 (labeled in FIG. 2). Catheter shaft 103 comprises a user grip 102 to which the distal end of interface cable 135 terminates. The proximal end of interface cable 135 terminates in an electrical catheter interface connector 136 which in turn interfaces with console 130. Irrigation source tube 137 also interfaces at its distal end with the proximal end of catheter interface cable 135 and provides irrigant to the ablation balloon sourced by the irrigation pump and irrigation reservoir 131 and 133 respectively. The irrigation system also comprises optional bubble and pressure sensors 139 and 138 respectively.

The console 130 additionally comprises a user interface 132 and an electronics component 134. The electronic component comprises a processor based control component, such as a microprocessor and associated ancillary hardware such as memory display drivers as typically comprised in a laptop, an RF power supply, associated circuitry to allow the processor component to control, drive, or read the state of the other electrically powered components including the pump, sensors, user interface, and RF power supply. The components comprised in the console have capabilities as described above.

The user interface 132 in FIG. 1 is capable of both presenting to and acquiring from the user information relevant to the use and control of the ablations system as delineated above. As illustrated here the user interface comprises a LCD touch screen. In alternate embodiments the user interface may comprise a keyboard. In other embodiments the processor component and user interface component may be embodied in a separate computing engine such as a typical laptop.

Balloon member 200 is designed to be inflated at its delivery location via the delivery of irrigant delivered from the reservoir 133 via pump 131 and associate plumbing.

Figure 2:
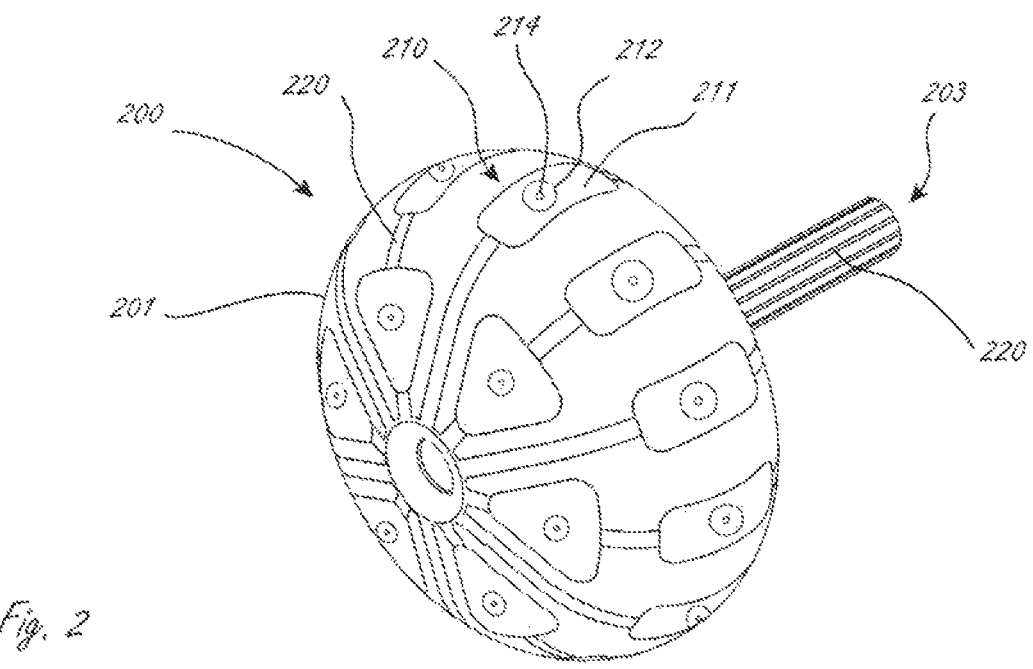
FIG. 2 illustrates an embodiment of the ablation balloon member of FIG. 1.

FIG. 2 illustrates the ablation balloon member 200 of FIG. 1 affixed to the distal end of catheter shaft 203 and some associated features including a plurality of multipurpose electrodes. The ablation balloon member comprises an expandable structure 201 comprising a balloon. Carried by the balloon is a plurality of multi-purpose electrodes 210. In some embodiments only some of the electrodes are multi-purpose electrodes while some are not.

Multi-purpose electrodes comprise variable impedance region 211 positioned to interface with adjacent tissues. The variable impedance regions 211 have impedances that decrease as a function of increased frequency. The multi-purpose electrodes also include low impedance region 212, which interfaces tissue, and has a relatively constant and low impedance. Associated with each electrode is also an irrigation aperture 214. In this embodiment the irrigation apertures are shown in the low impedance regions. The low impedance regions are also referred to herein as mapping regions. The low impedance regions plus the variable impedance regions are together referred to herein as the ablation regions of the electrodes. As illustrated, the total area for the distal ring of electrodes can be about approximately 30 $mm^2$, and the proximal ring can be about 26 $mm^2$. The low impedance portion of the electrodes can be approximately 4 $mm^2$.

Figures 3, 4A, 4B:
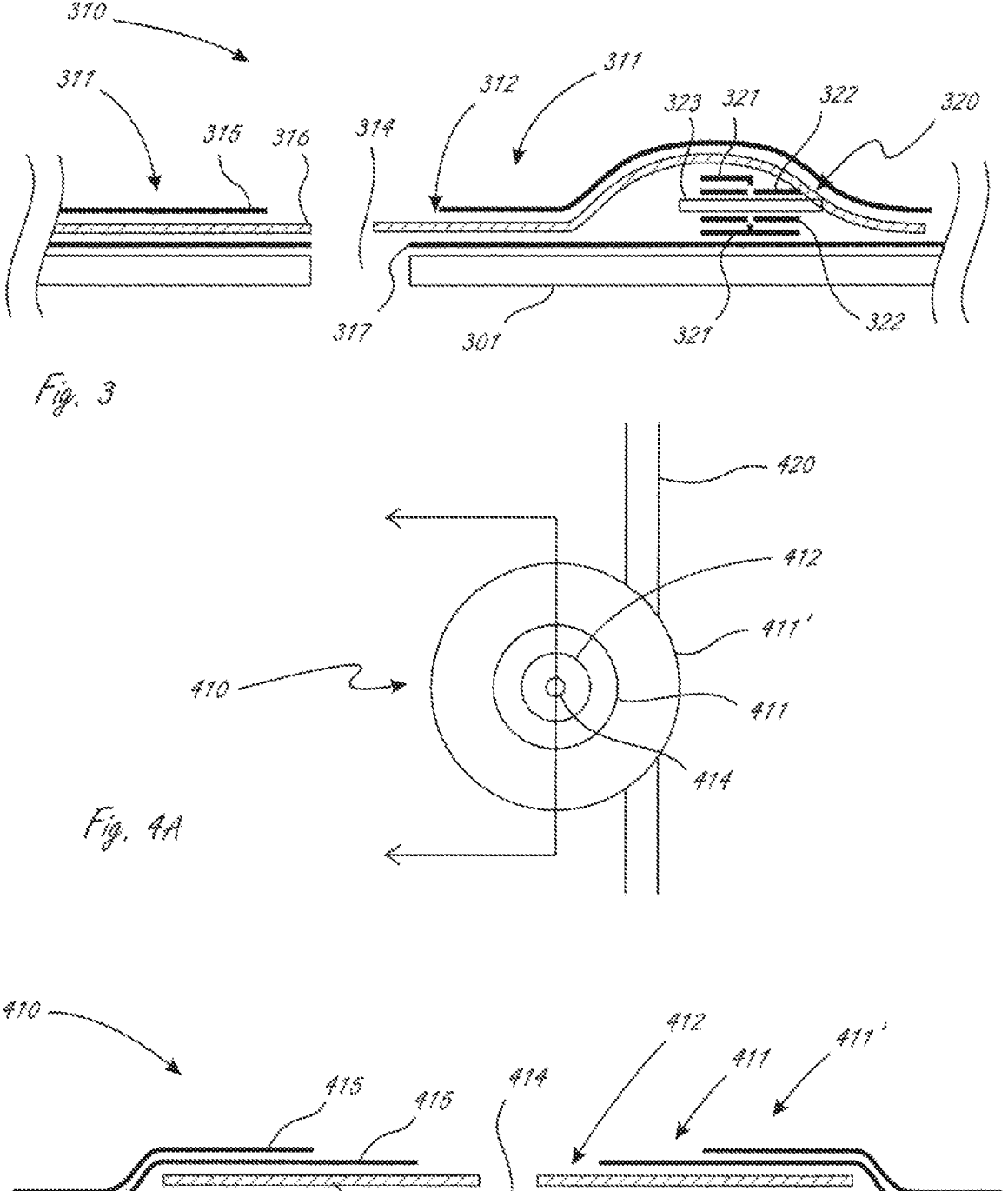
FIG. 3 illustrates a cross section of an embodiment of a multi-purpose electrode.
FIG. 4A illustrates another embodiment of a multi-purpose electrode.
FIG. 4B illustrates a cross section of the multi-purpose electrode shown in FIG.

FIG. 3 illustrates a cross section of an exemplary elastomeric multi-purpose electrode 310. The electrode is affixed to balloon 301. The layer closest to the balloon is an optional light absorbing or anti-reflection layer 317, particularly useful when an imaging system is used within the balloon to image features of the tissues adjacent to portions of the balloon. Overlaying layer 317 when present, or balloon 301 when 317 is not present, is an elastomeric electrode conductor layer 316. Such a layer may be comprised of a material such as a poly urethane suspension of silver particles as exemplified by but not limited to inks or conductive polymers made by the ECM corporation (Engineered Conductive Materials, LLC 132 Johnson Dr. Delaware, Ohio 43015). Overlaying a portion of the elastomeric electrode conductive layer 316 is a layer 315 of material comprising flexibility and relatively high dielectric constant. One such material comprises parylene N. The coating layer 315 can comprise a thickness of a few tenths of a micron to several microns. Other possible materials include polymeric based materials such as parylene or a Barium Titanate filled urethane. In other instances it can be composed of a layer of Titania applied directly to a metalized surface.

As depicted, the parylene layer 315 covers the majority of the elastomeric electrode conductive layer 316, but leaving a central region of the conductive layer, adjacent to and peripheral to the irrigation aperture 314, uncovered. Such a distribution of a dielectric layer as described creates a first region of frequency variable impedance 311, where region 311 is of a higher impedance and relatively frequency dependent, and a second region 312 which is of a lower impedance and relatively frequency independent. In the embodiment of multipurpose electrode 310 power is received via flex circuit 320. Region 312 is also referred to herein as a mapping region, and regions 312 and 311 combined are considered an ablation region. FIG. 3 illustrates region 312 comprising an inner portion of the electrode 310 surrounding aperture 314. In other embodiments region 312 can have different configurations, for example, region 312 can extend partway (e.g., about 25%, about 50%, about 75% around aperture 314). In other embodiments, the region 312 can be positioned at other locations on the electrode 310.

Flex circuit 320 comprises multiple conductors 322 typically comprising but not limited to copper. The conductors 322, 4 as illustrated, ride on a substrate layer 323 and are covered by insulation layers 321. Such a flex circuit is constructed from materials typically known and by means commonly known in the art of fabricating flex circuits. As illustrated in FIG. 3 the top right flex circuit conductor has no insulation 321 over it in a region beneath the elastomeric electrode conductive layer 316 thereby creating a low impedance interface between the two layers.

Figure 4C:
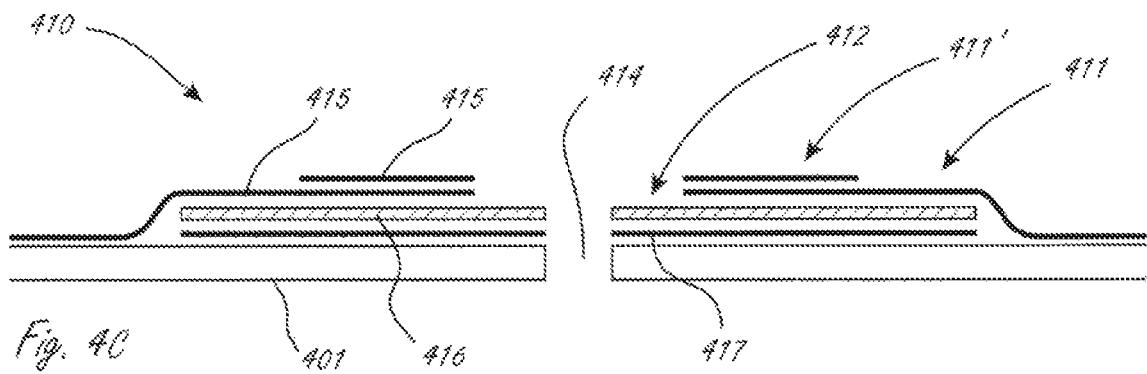
FIG. 4C illustrates another cross section for a multi-purpose electrode similar to that shown in FIG. 4A.

In some embodiments there may be more than one variable impedance region of a multi-purpose electrode. FIG. 4A illustrates an embodiment similar to that of FIG. 3, in which there are two variable impedance regions 411 and 411'. Outer variable impedance region 411' may be comprised of a thicker coating of the same material as that coating region 411 thereby requiring a higher frequency to attain the same relative impedance as that of 411. For example, outer variable impedance region 411' may comprise a thickness of about 0.2 micron and inner region 411 may comprise a thickness of about 0.1 micron. Alternatively, region 411' may be comprised of a thinner coating of the same material as that coating region 411 thereby requiring a lower frequency to attain the same relative impedance as that of 411 as illustrated in FIG. 4C. For example, outer variable impedance region 411' may comprise a thickness of about 0.1 micron, and inner region 411 may comprise a thickness of about 0.2 micron. In other alternative embodiments two different dielectrics may be used to create the two regions. Alternatively or in combinations, materials with different dielectric constants may be used to create areas with differing variable impedance characteristics. In yet other embodiments more continuous variations in thickness of material or dielectric constant may be fabricated. The multipurpose electrode of FIG. 4A is sourced by flex circuit 420 which continues past the multipurpose elastomeric electrode 410 to interface with additional electrodes.

FIG. 4B illustrates the cross section of the electrode shown in FIG. 4A.

Sections corresponding to the footprint of multipurpose electrodes on balloon 401 may be covered with optional backing layer 417, which in turn is covered by elastomeric electrode conductive layer 416. When layer 417 is not used, layer 416 may be applied directly to the balloon surface. Parylene layers 415 (or other suitable high dielectric constant materials) are then applied sequentially creating constant impedance section 412 (also referred to herein as mapping region), and variable impedance sections 411 and 411' (when combined with region 412 defines the ablation region). FIG. 4C illustrates an alternate cross section in which the thin variable impedance layer is on the outer periphery of the electrode.

Figure 5A:
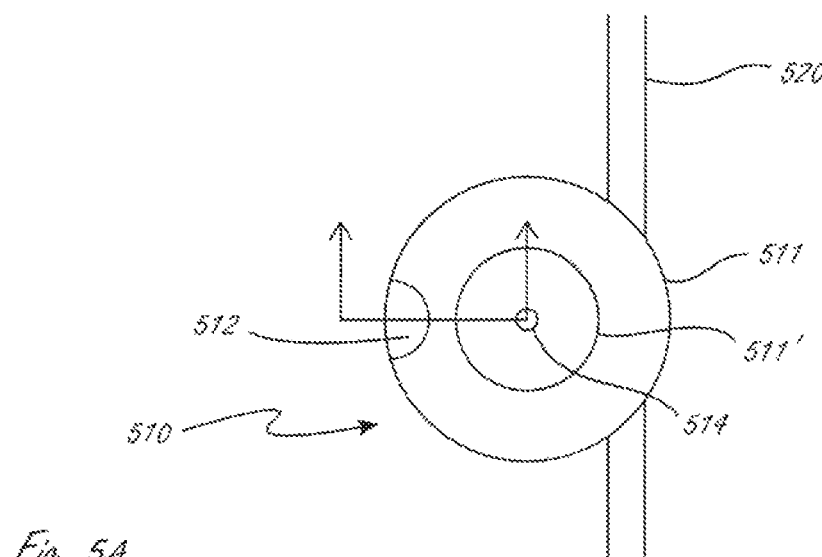
FIG. 5A illustrates an embodiment of a multipurpose electrode with a constant impedance section on the edge of the multipurpose electrode.
Figure 5B:
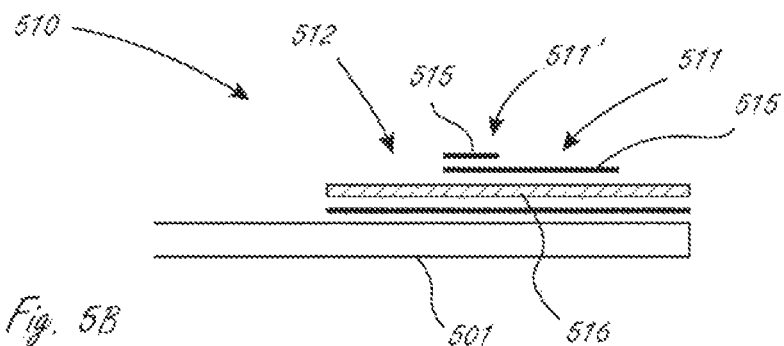
FIG. 5B illustrates a cross section of the multipurpose electrode illustrated in FIG. 5C.

In an alternate embodiment for a multipurpose electrode, illustrated in FIG. 5A and in a partial cross section in 5B, the constant impedance region 512 may be fabricated on the perimeter of the electrode 510. As shown, the constant impedance region 512 can comprise a round cutout shape positioned at one portion of the electrode 510. In other embodiments, the constant impedance region 512 can extend further along the perimeter of the electrode (e.g., along at least about 20%, about 50%, about 75%, or extending completely around the perimeter of the electrode). Electrode 510 interfaced with flex circuit 520 and comprising variable impedance region 511 and irrigation aperture 514.

Figure 6A:
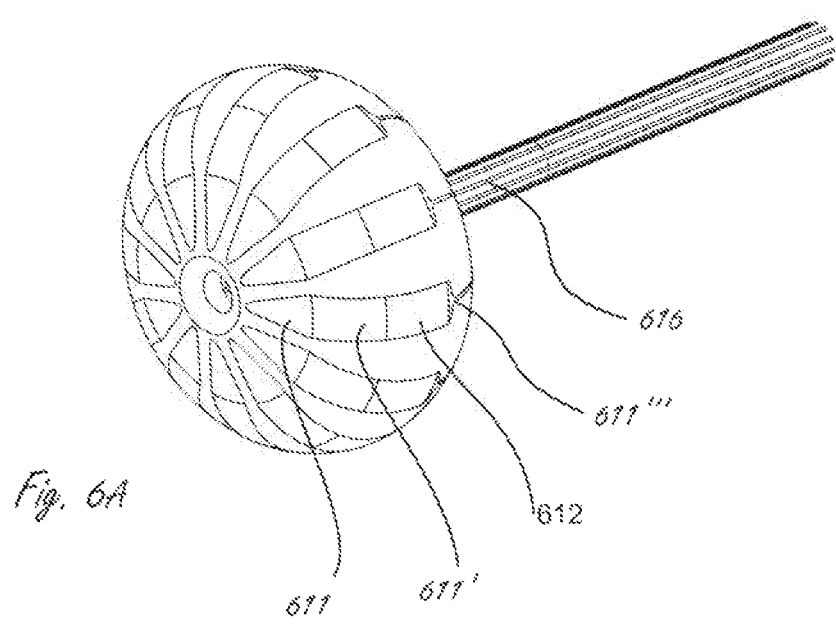
FIG. 6A illustrates another embodiment of an ablation balloon comprising multipurpose electrodes.
Figure 6B:
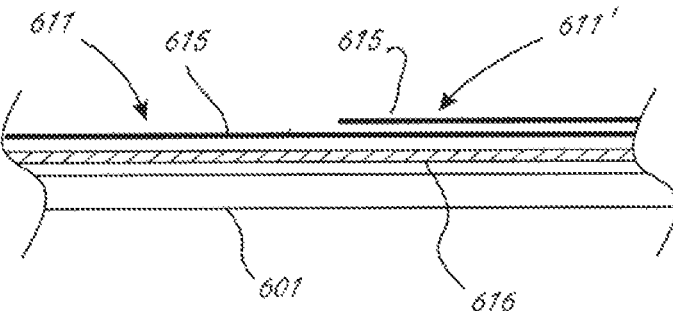
FIG. 6B illustrates an exemplary cross section for an electrode as illustrated in FIG. 6A.
Figure 6C:
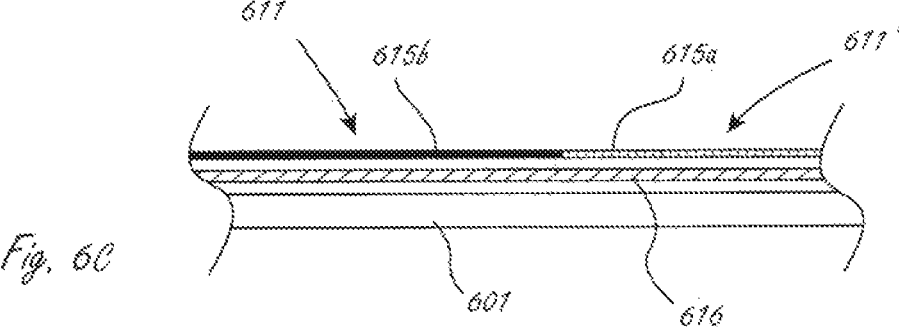
FIG. 6C illustrates an alternate exemplary cross section for an electrode as illustrated in FIG. 6A.

FIG. 6 illustrate an ablation balloon comprised of metalized electrodes and optionally conductors fabricated directly on the balloon by one of many known methods including but not limited to vapor deposition, electroless plating. These electrodes can then be covered by an elastomeric dielectric or a metal oxide dielectric as described elsewhere herein.

FIG. 6B illustrates a representative cross section of the multipurpose electrode comprising two regions 611, 611' with different thicknesses of dielectric material layered on a metalized electrode 616 applied to the surface of a balloon 601. Constant impedance section 612 is situated proximal to the variable impedance regions 611' and 611. Region 611''' is a conductor covered with the same dielectric 615 of even greater thickness. In one embodiment, the dielectric layer defining 611 may be one half the thickness of the dielectric layer defining region 611'. The dielectric material covering the conductor 611''' would be 10 or more times the thickness of that at 611. In other embodiments, the region 611 may have a greater thickness than region 611'. In yet another embodiment the dielectric layers 611 and 611' may be comprised of different materials with different relative dielectric values. One possible example is a layer of parylene N, with a relative dielectric constant of 2.65 at layer 615b and a layer of BaTiO3 filled urethane for layer 615a.

In some embodiments the balloon will be masked in areas where the high dielectric material is not desired. When parylene is used as the high dielectric material the masking material will be removed thereby removing that section of parylene in the process.

Alternatively, the high dielectric material may be removed by laser ablation.

High dielectric materials other than parylene may be used to create the variable impedance regions. Parylene is provided as an example. For example, in some embodiments BaTiO3 may be used in a urethane ink to create a material with a high dielectric constant of around 40 as compared with 3.65 for parylene N. In other embodiments, a gold or other metal coating may be applied directly to the balloon and the metal coated with TiO2 with a dielectric constant of approximately 80 at 1 MHz.

An embodiment of a method of using the multi-purpose electrodes described herein comprises advancing a balloon comprising a plurality of multi-purpose electrodes (e.g., electrode 310) to a site to be treated (e.g., atrial tissue around a pulmonary vein ostium). The electrode comprises a variable impedance region and a (relatively) constant impedance region. One or more of the electrodes is used to map the area to be treated and obtain low frequency (e.g., less than 1000 Hz) electrophysiological signals from the patient using the constant impedance region. Once the position of the ablation balloon has been verified based on the data obtained during the mapping phase, both the variable and constant impedance regions can be used to ablate tissue by applying an electrical signal at an ablation frequency of at least about 50 KHz thereto.

What is claimed is:

1. An electrode for use with an ablation catheter including a balloon having an irrigation aperture, the electrode comprising:
   a conductive polymer layer coupled to the balloon and having an inner surface facing toward the balloon and an outer surface facing away from the balloon, the conductive polymer layer defining an irrigation aperture; and
   an outer layer of dielectric material disposed radially outward from the conductive polymer layer in a direction extending from a center of the balloon and having a thickness, the outer layer of dielectric material defining an opening larger than the irrigation aperture, so as to define an overlap region where the outer layer overlaps the conductive polymer layer and a non-overlap region adjacent to the irrigation aperture where the conductive polymer layer is exposed;
   wherein the overlap region defines a variable impedance region having a first exposed surface area, wherein the variable impedance region has a first impedance when a first electrical signal having a first frequency is applied thereto, and a second impedance when a second electrical signal having a second frequency is applied thereto, the second impedance being different than the first impedance; and
   wherein the non-overlap region defines a substantially constant impedance region having a second exposed surface area less than the first exposed surface area of the variable impedance region;
   wherein the thickness of the outer layer of dielectric material is such that the overlap region conducts an ablation energy at the second frequency through the entirety of the outer layer so as to treat tissue with the ablation energy.

2. The electrode of claim 1, wherein the first impedance is higher than the second impedance when the first electrical signal has a lower frequency than the second electric signal.

3. The electrode of claim 1, wherein the first electrical signal has a frequency of about 1000 Hz or less, and the second electrical signal has a frequency of at least about 50 KHz.

4. The electrode of claim 1, wherein the substantially constant impedance region is adapted so that an impedance of the substantially constant impedance region does not vary based on the frequency of an electrical signal applied thereto.

5. The electrode of claim 1, wherein the non-overlap region is disposed in a central portion of the electrode.

6. The electrode of claim 1, wherein the overlap region is disposed in a peripheral region of the electrode.

7. The electrode of claim 1, wherein the variable impedance region includes a layer of high dielectric material.

8. The electrode of claim 1, wherein the electrode includes more than one variable impedance region.

9. The electrode of claim 1, wherein the variable impedance region is disposed in a peripheral region of the electrode.

10. The electrode of claim 1, wherein the substantially constant impedance region is disposed within a central portion of the electrode.

11. The electrode of claim 1, wherein the electrode is individually addressable.

12. The electrode of claim 1, wherein a periphery of the electrode defines an uninterrupted electrode surface area that can be exposed to tissue to deliver an electrical signal to the tissue.

13. The electrode of claim 1, wherein the substantially constant impedance region has an impedance lower than the first impedance or the second impedance.

14. The electrode of claim 1, wherein the electrode is configured to pass ablation energy at an ablation frequency through its entirety.

15. An electrode comprising:
   a physiological signal mapping section comprising a substantially constant impedance region having a constant impedance surface area; and
   a tissue ablating section comprising the substantially constant impedance region and a variable impedance region having a variable impedance surface area greater than the constant impedance surface area, wherein the variable impedance region has a first impedance when a first frequency is applied thereto, and a second impedance when a second frequency is applied thereto, the second impedance being different than the first impedance,
   wherein the variable impedance region includes a first layer of material disposed radially outward in a direction extending from a center of a conductive polymer conductive electrode layer of material coupled to a balloon, the first layer of material having a thickness,
   wherein the thickness is such that the variable impedance region conducts an ablation energy at the second frequency that passes through the first layer so as to treat tissue with the ablation energy, and
   wherein the first layer defines an opening such that the first layer overlaps with only a portion of the conductive polymer electrode layer of material, to create an overlap region defining the variable impedance region where the first layer and the conductive polymer electrode layer overlap, and a non-overlap region defined by the opening and defining the substantially constant impedance region where the first layer and the conductive polymer electrode layer do not overlap.

* * * * *